United States Patent [19]

Schachar

[11] 4,390,542
[45] Jun. 28, 1983

[54] METHOD FOR INHIBITING CONTRACTION OF OPTHALMIC WOUNDS OR INCISIONS

[76] Inventor: Ronald A. Schachar, P.O. Box 145, Denison, Tex. 75020

[21] Appl. No.: 212,315

[22] Filed: Dec. 2, 1980

[51] Int. Cl.³ .................. A61K 31/485; A61K 31/52; A61K 31/445; A61K 31/365

[52] U.S. Cl. .................................... 424/260; 424/253; 424/267; 424/301; 424/309; 424/317; 424/330

[58] Field of Search ............... 424/258, 260, 253, 267, 424/301, 309, 317, 330

[56] References Cited

U.S. PATENT DOCUMENTS 2,390,555  12/1945  Richardson ......................... 544/158
3,910,927  10/1975  Kreighbaum et al. ............... 424/258
4,018,927   4/1977  Voorhees ............................ 424/260

OTHER PUBLICATIONS

Science 173 (996), pp. 548–550, (1971)–Majno et al., "Contraction of Granulation Tissue in Vitro . . . ", Chem. Abst. 69 103502(u) (1968)–Bernat.

Primary Examiner—Douglas W. Robinson
Attorney, Agent, or Firm—Thomas R. Boland

[57] ABSTRACT

Method for controlling the contraction of ophthalmic wounds or incisions by administering through an ophthalmalogically acceptable composition including a smooth muscle relaxant such as papavarine. The method also encompasses the administration to such wounds or incisions of a smooth muscle stimulant such as Seratonin.

7 Claims, No Drawings

METHOD FOR INHIBITING CONTRACTION OF OPTHALMIC WOUNDS OR INCISIONS

BACKGROUND OF THE INVENTION

This invention relates to a method for controlling the contraction of wounds or incisions made in the eye, especially non-penetrating incisions in the cornea. The contraction of open wounds has been established as a function of contractal fibroblasts known as myofibroblasts, i.e., cells combining the electron microscopic features of fibroblasts and smooth muscle cells which, pharmacologically and immunologically, have many features of smooth muscle.

The influence of such cells on wounds or incisions in human skin has been studied but their presence in the eye, where they could be an important factor in retarding the success of certain operations, have not previously been determined.

Recently a procedure has been proposed for the surgical correction of complex myopic astigmatism by anterior keratotomy (see, Fedorov, S. N., et al., *Oftalmologischeskii Zhurnal* (Odessa) 34(4):210-2 (1979); Utkin, V. F., *Vestnik Oftalmologii* (Moskna), (2):21-4 (1979)). This procedure involves making a series of radial, non-penetrating incisions on the periphery of the cornea, whereby the cornea is weakened so as to induce an alteration in its curvature. Consequently, the cornea becomes flatter thereby altering its optical power and substantially correcting the myopic condition. In the initial stages of this procedure the flattening of the cornea occurs partially because of edema, i.e., the adsorption of water into the cornea which causes it to swell. Within approximately two weeks the edema subsides but a regression of the flattened condition in the cornea continues for about four months. Since flattening of the cornea effects correction of the myopic condition, the post-operative process of regression is counterproductive to the intended results of the procedure.

It has now been discovered that the contraction of such ophthalmic wounds and incisions can be controlled during the healing process and regression inhibited according to the present method which will be described in detail below.

SUMMARY OF THE INVENTION

In accordance with this invention, the contraction of ophthalmic wounds or incisions can be controlled by administering thereto an effective amount of an ophthalmalogically acceptable, pharmaceutical composition comprising a smooth muscle relaxant or a smooth muscle stimulator in proportions which are respectively effective in inhibiting the contraction of myofibroblasts therein or in substantially re-establishing a desired configuration in the wound or incisions following administration of the relaxant. This method is particularly useful in preventing the contraction of incisions in anterior radial keratotomy so as to prevent regression of the cornea from its expanded and flattened configuration.

DETAILED DESCRIPTION OF THE PREFERRED EMBODIMENTS

For the purposes of this specification and claims, an effective amount of smooth muscle relaxant will be that amount which inhibits the contraction of myofibroblast in ophthalmic wounds or incisions. An effective amount of a smooth muscle stimulant will be that amount which substantially re-establishes a desired configuration of the wound or incision following administration of the smooth muscle relaxant. The administration of the smooth muscle stimulant will be indicated only in those instances where there is an inadvertant over-dosing of the smooth muscle relaxant.

Among the smooth muscle relaxants (spasmolytics) which are useful in this invention are papaverine, trocinate, oxybutynin chloride, flavoxate hydrochloride, prostaglandin E, cyctochalasine B, alverine citrate, theophyllines and adiphenine, although papaverine hydrochloride is preferred (for a review of the commercial synthesis of papaverine see Goldberg, *Chem. Prod. Chem. News* 17, 371 (1954); see U.S. Pat. No. 2,390,555 for preparation of trocinate).

Among the smooth muscle stimulants which may be used in accordance with this invention are, for example, Seratonin (5-hydroxytryptamine, see U.S. Pat. No. 2,717,129 for synthesis).

The smooth muscle relaxants or stimulants used in practicing the method of treatment in this invention may be applied to the eyes by any known means, although in the preferred form they are topically applied to the eye, e.g., by instillation of a solution of the active ingredient in a suitable, non-toxic, ophthalmic vehicle. Where maximum penetration of the active ingredient into the cornea is desired, a vehicle such as dimethylsulfoxide, for example, may be employed. Essentially any conventional solution forming technique may be utilized in preparing the ophthalmic solutions of this invention. Aqueous ophthalmic solutions may be formulated, for example, in accord with the procedures set forth in Chapter 83 of Remington's Pharmaceutical Sciences, 14th Edition, Mack Publishing Company. As such, they are sterile and may contain bacteriological preservatives to maintain sterility during use.

For most purposes, the addition of benzalkonium chloride to the ophthalmic solution provides the desired biocidal preservative effect. However, additional biocides may be incorporated, if desired. For example, it is generally desirable to incorporate a suitable chelating agent to enhance the preservative effect of the benzalkonium chloride. Suitable chelating agents include di-, tri-, or tetrasodium ethylene diamine tetracetate, also known as edetates, with disodium edetate being a preferred ingredient. Other biocides that may be optionally included in the ophthalmic solution include thimerosal, phenylmercuric nitrate, chlorobutanol, and sorbicacid.

For most ophthalmic uses it is desirable that the ophthalmic solution be isotonic. Conventionally, ophthalmic solutions are rendered isotonic by addition of suitable salts, for example, sodium chloride, potassium chloride, calcium chloride, magnesium chloride, and various nitrates, citrates, acetates, etc. Preferably, monovalent salts such as sodium chloride and the like are added in an amount sufficient to give a freezing point depression or osmotic pressure equivalent to that provided by 0.5% to 1.5% sodium chloride.

If desired, the ophthalmic solutions utilized in this invention may be adjusted in pH by one or more of the acids or bases known for use in ophthalmic solutions. The ophthalmic solutions may be maintained in an acidic, basic, or neutral condition by use of buffers commonly employed in ophthalmic solutions. The use of suitable acids, bases and buffering systems to establish a pH within the range of from about 3.0 to about 8.5 is well known and requires no further description. Typically, the pH of the ophthalmic solutions utilized in this invention is between about 5.0 and 8.0, preferably between about 6.0 and about 7.5.

The viscosity of the ophthalmic solutions used in the present invention may be adjusted to a point within the range of from about 1 cps to about 25 cps at 25° C. (The viscosity of the ophthalmic solutions are measured on a Wells-Brookfield Microviscometer (cone and plate) Model LVT). Such an adjustment can be made by inclusion of water-soluble viscosity building agents. Suitable viscosity building agents include natural gums, such as guar gum and gum tragacanth; gelatin; starch derivatives; polymeric glycols; and cellulosic polymers, such as hydroxyethylcellulose, hydroxypropylcellulose, emthylcellulose, hydroxyropylmethylcellulose, and carboxymethylcellulose. Viscosity building agents, when used, are present in such ophthalmic solutions at a level of from about 0.001% to about 1.0% by weight. The exact percentage depends on the molecular weight of the polymer used which is within the skill of the art. When a viscosity building agent is utilized, the viscosity of the ophthalmic solution may be between about 1 cps and about 25 cps, preferably between about 3 cps and about 15 cps.

Ointments may also be employed as vehicles for the active ingredients used in the treatment of this invention. Such ointments may be prepared utilizing known pharmaceutical techniques with conventional petrolatum vehicles.

The ophthalmologically effective amounts of smooth muscle relaxant or stimulant used in accordance with this invention will vary depending on the potency of the selected active ingredient. Where known smooth muscle relaxants or stimulants are utilized, such as the preferred relaxant papaverine, or stimulant Serotin, the effective amount is readily ascertained by one skilled in the art from simple experiments. By way of example, when utilizing papaverine hydrochloride as the active ingredient, the preferred concentration thereof in aqueous solution will be about 1% to about 2% by weight. Such a solution will be topically administered to humans in a dosage of 1-2 drops per eye, every four hours during the awake periods of the healing process, i.e., for about four months. Preferably, the application of the solutions utilized in this invention will be in drop form in the manner typically used to apply eye drops. Thus, the normal squeeze-type liquid drop application devices are perfectly suitable for use in applying the ophthalmic solutions of this invention to an eye intended for treatment.

It should be understood that this invention may be embodied in other specific forms without departing from its spirit or essential characteristics. Accordingly, the present embodiments are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A method for inhibiting contraction of an ophthalmic wound or incision which comprises administering to said wound or incision a pharmaceutically acceptable composition comprising an ophthalmological carrier and an effective amount of smooth muscle relaxant to inhibit the contraction of myofibroblasts present in the wound or incision.

2. The method of claim 1 wherein said composition is an aqueous solution.

3. The method of claim 2 wherein said solution is isotonic and contains a biocidal preservative.

4. The method of claim 1 wherein said smooth muscle relaxant is papaverine hydrochloride.

5. The method of claim 4 wherein the composition comprises an aqueous solution containing about 1% to about 2% by weight of papaverine hydrochloride.

6. A method of preventing contraction of eye incisions made in anterior radial keratotomy, comprising administering to the incisions an effective amount of a smooth muscle relaxant to arrest the contraction of myofibroblasts in said incisions.

7. The method according to claim 6 wherein the smooth muscle relaxant is papaverine hydrochloride.

* * * * *